United States Patent [19]
Ryan

[11] Patent Number: 5,336,179
[45] Date of Patent: Aug. 9, 1994

[54] LINE ORGANIZER

[76] Inventor: Richard M. Ryan, 19326 Lemarsh St., Northridge, Calif. 91324

[21] Appl. No.: 155,297

[22] Filed: Nov. 22, 1993

Related U.S. Application Data

[63] Continuation-in-part of Ser. No. 69,504, Jun. 1, 1993.

[51] Int. Cl.⁵ .......................... A61M 5/14; A61M 5/00
[52] U.S. Cl. ...................................... 604/80; 604/258; 128/DIG. 26; 128/DIG. 6
[58] Field of Search ............... 128/DIG. 6, DIG. 26; 604/80, 81, 250, 258, 283, 284, 261, 189, 191; 248/65, 68.1, 70, 72, 74.2, 205.2, 206.5, 228–230, 231.5, 213.8

[56] References Cited

U.S. PATENT DOCUMENTS

| | | | |
|---|---|---|---|
| 1,558,770 | 10/1925 | Andersen | 248/231.5 |
| 1,688,765 | 10/1928 | Veras | 248/231.5 |
| 3,210,816 | 10/1965 | Clemons | 128/DIG. 26 X |
| 4,141,524 | 2/1979 | Corvese, Jr. | 248/70 |
| 5,224,674 | 7/1993 | Simons | 604/80 |

*Primary Examiner*—C. Fred Rosenbaum
*Assistant Examiner*—Frank Wilkens
*Attorney, Agent, or Firm*—Jack C. Munro

[57] ABSTRACT

An organizer for organizing and maintaining a plurality of lines in a specifically arranged manner. The organizer is to include a clamping arrangement to facilitate securement to an exterior structure. The lines are fixedly mounted at appropriate spaced-apart locations on a block with this block being pivotally mounted on the clamping apparatus so as to position the lines at a desired orientation relative to an exterior structure upon which the clamping apparatus is mounted. Identifying indicia is to be placed on the organizer which is to correspond to identifying indicia on the lines so as to organize the lines and avoid confusion between the different lines mounted on the organizer.

8 Claims, 3 Drawing Sheets

LINE ORGANIZER

REFERENCE TO PRIOR APPLICATION

This application is a continuation-in-part of patent application Ser. No. 08/069,504, filed Jun. 1, 1993, by the same title and same inventor, now pending.

BACKGROUND OF THE INVENTION

1. Field of the Invention

The field of this invention relates to apparatus for neatly organizing a variety of objects and more particularly to an apparatus which neatly holds a plurality of flexible lines in conjunction with an exterior structure.

2. Description of the Prior Art

The subject matter of this invention will be discussed primarily in conjunction with flexible lines in the form of fluid-conducting tubes that are commonly used within the medical profession. However, it is considered to be within the scope of this invention that the apparatus of the invention could be utilized in conjunction with lines other than tubes, such as for example electrical wires.

During the course of medical procedures, a human patient is often infused simultaneously with a plurality of different medications and fluids. Those medications and fluids are fed into the patient through tubes. Additionally, catheters are frequently utilized to monitor body functions. Many of these catheters, fluid-conducting tubes and even monitoring lines are placed on the patient even prior to when the patient is transported from a surgery area to a convalescing area. These different lines have a tendency to become entangled, making it difficult for attending physicians and nurses to ascertain which line is being utilized for which purpose. At times certain medicines are injected into a fluid line. Extreme care has to be exercised to make sure that the right medicine is being injected into the correct line. This problem of confusing lines and catheters entering a patient's body is accentuated under emergency conditions. There is a further problem and that is that excessive stress is caused on the lines themselves which can cause the lines to become disconnected. The foregoing problems increase the risk of patient injury by either infusing medicine or blood at the wrong entry site, or by failure to infuse needed medications.

This entanglement of the different lines is exceedingly common in the hospital room while the patient is recovering from a surgical operation. This entanglement is caused primarily by the patient moving around in either a conscious or unconscious condition. There is a need within the hospital room to construct a device to which the different lines that are connected to the patient can be located, with this device keeping the different lines separate and unentangled and also making it easy for the physician and nurse to determine which line is which.

SUMMARY OF THE INVENTION

The structure of the present invention relates to an organizer in the form of a resilient block which includes a plurality of spaced-apart parallel slots. Each slot is configured so as to snappingly receive a line such as an electrical monitoring line, a catheter line or a liquid-conducting tube. There is numerical indicia mounted on the block with there being a different number for each slot. Corresponding indicia is to be placed on the different lines so that when a line is associated with a particular slot, that the indicia between that line and the slot will coincide. The block is pivotable to any desired position on a clamping apparatus. The pivoting of the block is for the purpose of altering orientation of the lines as such is desired. The clamping apparatus can take any of numerous forms with the generic form comprising a pair of jaws that are expandable to an open position, and when closed, are snugly clamped on to an exterior structure such as a bed rail. Another version of the clamping apparatus would be a strap assembly that can be tightened onto the bed rail. A further version of this invention is to mount the block on a handle of the clamping apparatus.

It is the primary objective of the present invention to provide an apparatus for organizing lines in a manner where the lines are transversely firmly retained in an organized configuration, but permitting longitudinal movement.

Another objective of the present invention is to construct a line organizer which facilitates connection and disconnection of the lines to and from the organizer, but yet retains the lines in conjunction with the organizer when the lines are connected thereto.

Another objective of the present invention is to construct an organizer which can be securely mounted on a wide variety of different configurations of exterior structures and thereby is not limited to a single configuration of exterior structure such as a cylindrically-shaped bed rail.

DETAILED DESCRIPTION OF THE SHOWN EMBODIMENT

Figure 1:
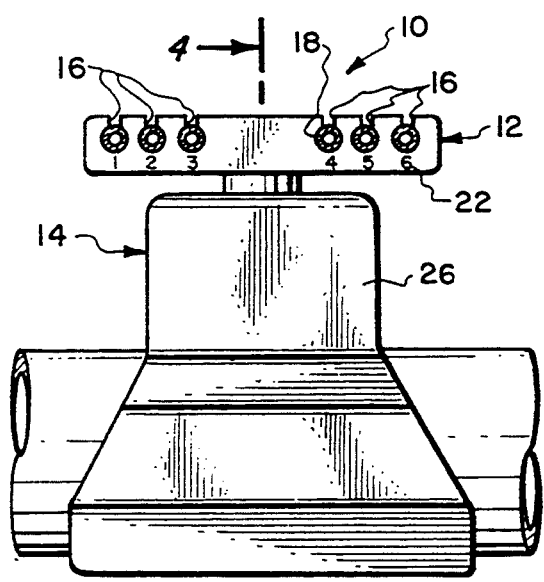
FIG. 1 is a side elevational view of the first embodiment of a line organizer of this invention.

Referring particularly to the drawings, there is shown the first embodiment 10 of the line organizer of this invention. Generally the line organizer 10 is constructed of a block 12 and a clamping apparatus 14. Block 12 will normally be constructed of a plastic or rubber material with it being important that the material for construction will permit a certain amount of slight deflection. Formed within the block 12 are a plurality of slots 16. Slots 16 are spaced apart and are located in a parallel relationship. Slots 16 are open ended. The slots 16 can be of the same cross-sectional size or can be of different cross-sectional sizes.

Each slot 16 defines a lower enlarged section, generally circular, and a necked-down area providing access into the lower enlarged section. A tube 18 is to be placed within a slot 16 in a close fitting manner. Actually the tube 18 is forcibly inserted through the necked-down area of the slot 16 with this necked-down area slightly expanding during the insertion process. After the tube 18 has passed the necked-down area of the slot 16, the tube 18 will be closely retained within the lower enlarged section of the slot 16. Longitudinal sliding movement of the tube 18 relative to slot 16 will be permitted.

It is to be understood that the tube 16 can include liquid-conducting tubes, wires, catheters and any other desired type of line. The tubes 18 are to be conducted from a source (not shown) to a terminating location (not shown). A typical terminating location would be a human convalescing from a surgical procedure. Typical sources would be an electronic monitoring apparatus or intravenous bottle. It is to be understood that normally there will be only one line 18 from a single source.

Figure 2:
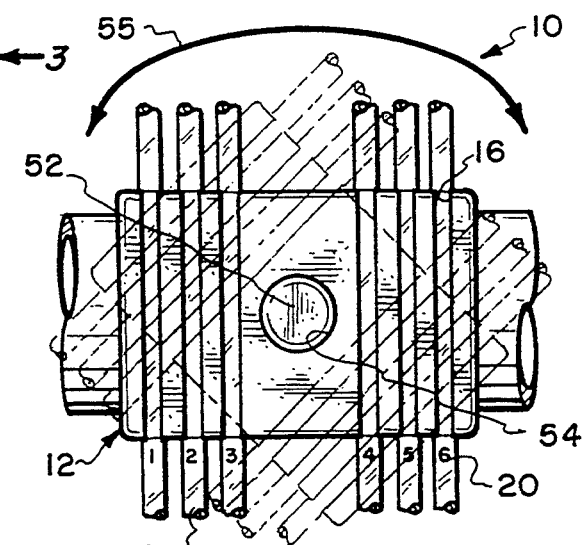
FIG. 2 is a top plan view of the line organizer of FIG. 1 depicting the pivotable motion of the block portion of the organizer relative to the clamping apparatus of the organizer.

In order to organize the different lines 18, each line 18 may include a label with indicia in the form of a plurality of numbers 20. In referring FIG. 2 of the drawings, it can be seen that the lines 18 are numbered between 1 and 6. Similar numerical indicia 22 is placed on the side wall of the block 12. The numerical indicia 22 is to be arranged so that the number 1 is located directly adjacent one of the slots 16 and the number 2 is located directly adjacent the next adjacent slot 16, and so forth until all six slots 16 are numbered. Line 18, that is numbered 1, is to be placed within the slot 16 that is also numbered 1. The same goes true for the remaining lines 18. The result is that the physician or nurse can readily observe which line connects between, for example, an intravenous bottle to a needle that is applied within the correct arm of the patient. Let is be assumed also that the nurse or physician desires to inject a medicine into that location. The physician or nurse then only needs to find that line by its number and then that person knows that the correct line has been found for the injecting of the medicine.

Clamping apparatus 14 takes the form of a pair of jaws 24 and 26. Jaws 24 and 26 are basically identical to each other and are generally located in a facing relationship forming a clamping section 28 there between. A portion of each of the jaws 24 and 26 within the clamping section 28 are covered with a frictional layer 30 material such as a soft rubber. The layers 30 are for the purpose of establishing a tight frictional engagement to an exterior structure such as the cylindrically-shaped bed rail 32 shown in FIG. 3 or the rectangularly-shaped bed rail 34 shown in FIG. 4.

Figure 3:
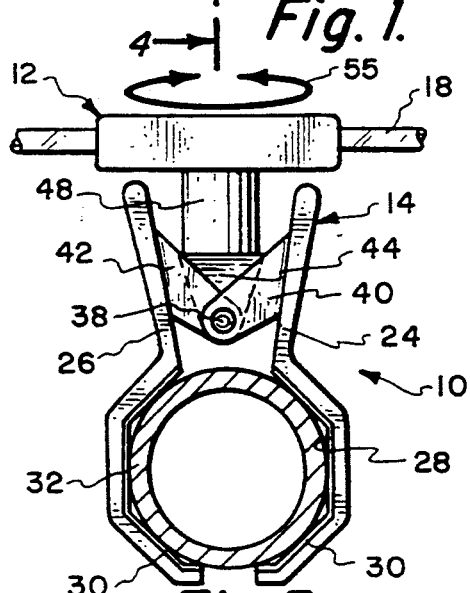
FIG. 3 is a front view of the line organizer of the present invention taken along line 3—3 of FIG. 1 showing the bed rail exterior structure upon which the organizer is mounted in cross-section.
Figure 4:
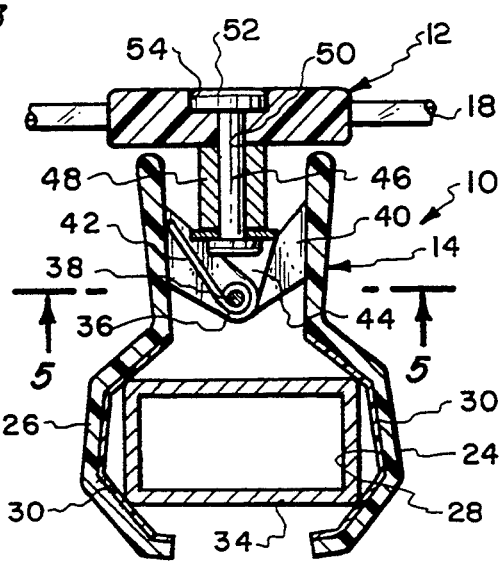
FIG. 4 is a view similar to FIG. 3, but showing the line organizer being connected to a rectangularly shaped bed rail as opposed to the cylindrically shaped bed rail of FIG. 3.
Figure 5:
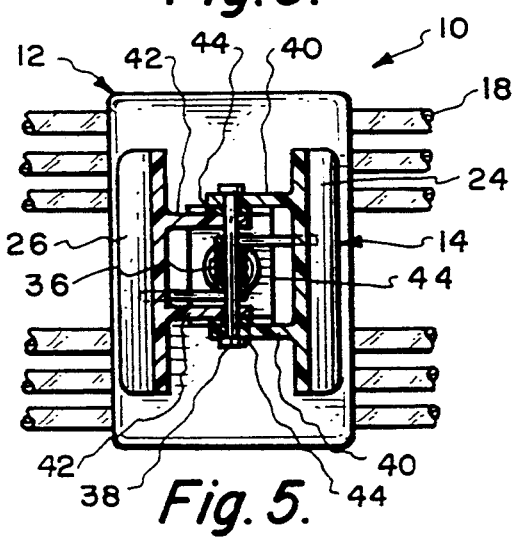
FIG. 5 is a cross-sectional view through the clamping apparatus of the first embodiment of the line organizer of this invention taken along line 5—5 of FIG. 4.
Figure 6:
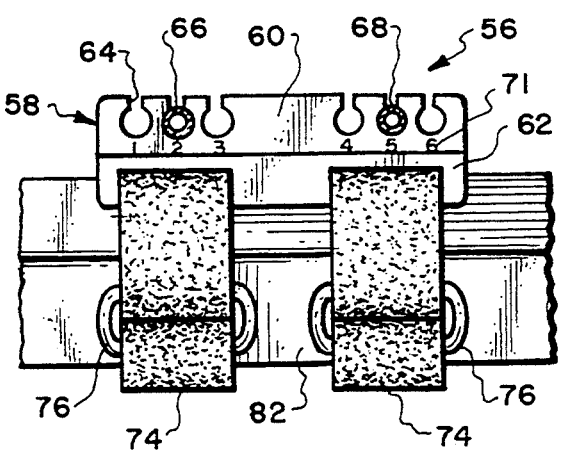
FIG. 6 is a side elevational view similar to FIG. 1 but of a second embodiment of the line organizer of this invention.
Figure 7:
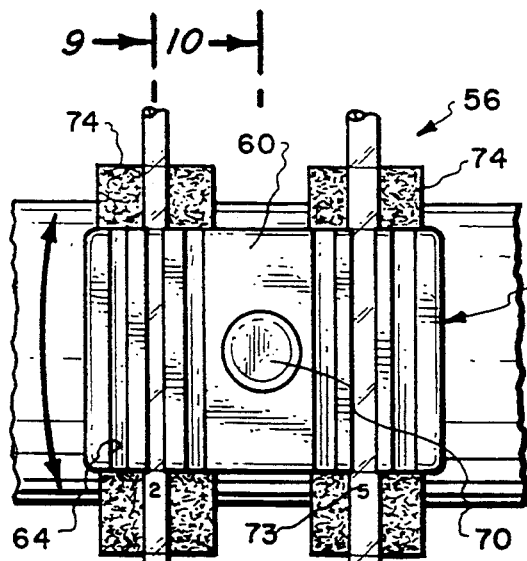
FIG. 7 is a top plan view of the line organizer of FIG. 6.
Figure 8:
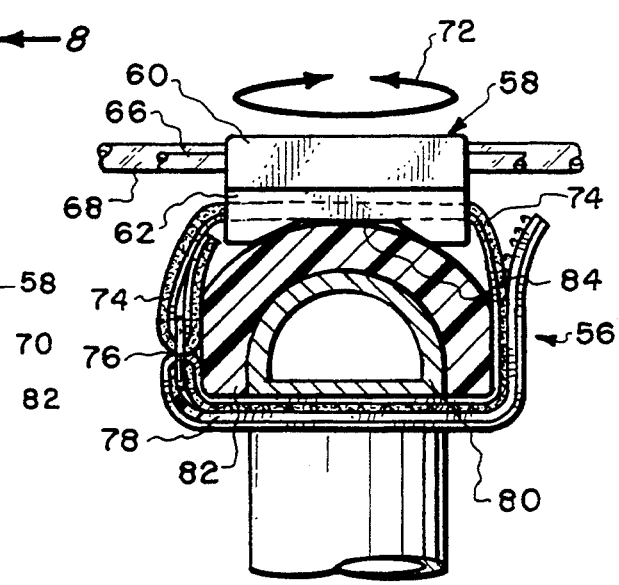
FIG. 8 is a front view of the second embodiment of the line organizer of this invention taken along line 8—8 of FIG. 7 showing a still further different configuration of exterior structure bed rail on which the line organizer has been mounted.
Figure 9:
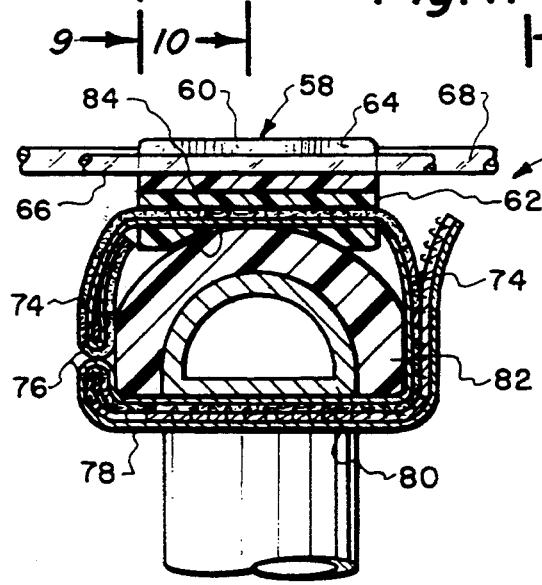
FIG. 9 is a cross-sectional view taken along line 9—9 of FIG. 7.
Figure 10:
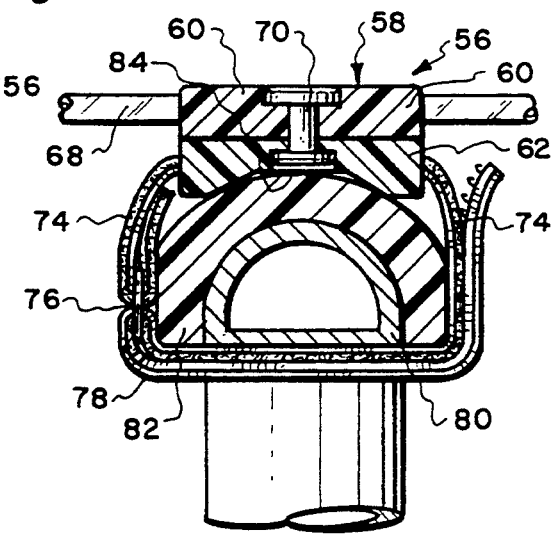
FIG. 10 is a cross-sectional view taken along line 10—10 of FIG. 7 showing clearly the pivotable connection between the block and the clamping apparatus of the second embodiment of the line organizer of this invention.

The jaws 24 and 26 include upper ends that are capable of being manually moved toward each other. When manually moved toward each other, the jaws 24 and 26 are moved to an unsecured position. When manual force is not applied to the handle section of the jaws 24 and 26, a coil spring 36 forces the jaws 24 and 26 into the secured position, tightly engaging the bed rail 32 or 34, as is shown in FIGS. 3 and 4. The coil spring 36 is mounted on a pin 38. One end of the spring 38 physically contacts the jaw 24 and the opposite end of the spring 38 physically contacts the jaw 26. The bias of the spring 36 is selected so that the jaws 24 and 26 will be constantly biased toward the secured position.

The pin 38 is mounted within aligned holes formed within a pair of bifurcated plates 40 integrally connected to the inside surface of the handle section of the jaw 24. The pin 38 also passes through holes formed within bifurcated plates 42 integrally formed on the inside surface of the jaw 26.

Also mounted on the pin 38 are a pair of spaced-apart legs of a base 44. Between the legs of the base 44 there is conducted a rivet 46. This rivet 46 is conducted through a sleeve 48 and through a hole 50 formed in block 12. The outer or upper end of the rivet 46 is formed into a head 52 with this head 52 resting within recess 54 of the block 12.

Because of the rivet 46, the block 12 is capable of being pivoted relative to the clamping apparatus 14. This pivoting of the block 12 is depicted by arrow 55 in FIG. 2 and is so as to orient the position of the lines 18 in any desired location.

Referring particularly to FIGS. 6 to 10 of the drawings there is shown a second embodiment of the line organizer of this invention. The second embodiment 56 includes a block 58 which is somewhat different than block 12 in that block 58 is composed of an upper part 60 and a lower part 62. Formed within the upper surface of the upper part 60 are a plurality of parallel slots 64 which are essentially identical to the slots 16. Connectable to each of the slots 64 is a line such as lines 66 and 68. It is to be noted that line 68 is of a slightly larger diameter than line 66 to show that the embodiments of this invention could be utilized to organize and retain different sizes of lines. The lines 66 and 68 will include appropriate numerical indicia 80 with similar such indicia also being inscribed on the upper part 60 which is not shown. Interconnecting the upper part 60 and the lower part 62 is a rivet 80 with this rivet 80 permitting adjusting pivotal movement of the part 60 relative to part 62, as is depicted by arrow 72 in FIG. 8.

Fixedly connected to the part 62 is a pair of spaced-apart upper straps 74. One end of the strap 74 is formed into a loop and is connected with a buckle 76. Buckle 76 connects with a lower strap 78. The outer end of the lower strap 78 is to include a male section of a fastener that is commonly sold under the trade name of Velcro ®. An appropriate female section for the fastener is to be mounted on the portion of the strap 74 that is connectable with the male portion of the fastener.

A half moon-shaped bed rail 80 is shown in FIGS. 8, 9, 10 and 12. On this half moon-shaped bed rail 80 is mounted an armrest 82 with this armrest only being shown in FIGS. 8, 9 and 10. The armrest 82 generally comprises some type of a soft covering, such as a rubber or plastic. The straps 74 and 78 can be connected together about the armrest 82 in a snug manner with the upper domed area of the armrest 82 resting within recess 84 formed within the bottom surface of the part 62. Straps 74 and 78 can be tightened as much as desired to make sure that the embodiment 56 is snugly retained on the armrest 82.

Possibly in some installations there will not be an armrest 82 but merely the bed rail 80. In such an instance the straps 74 and 78 can be similarly secured about the half moon-shaped (actually, any shaped) bed rail 80, as is clearly shown in FIG. 12.

Figure 11:
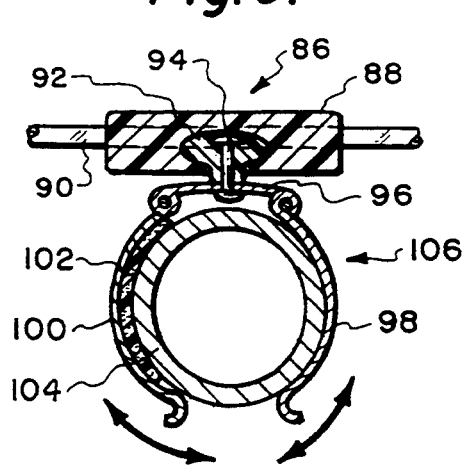
FIG. 11 is a cross-sectional view similar to that of FIG. 10 but of a third embodiment of the line organizer of this invention.
Figure 12:
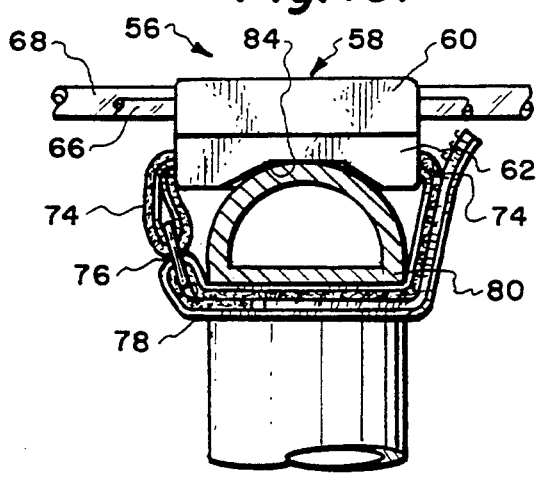
FIG. 12 is a view similar to FIG. 8 but showing the second embodiment of the line organizer being mounted directly on the bed rail as opposed to being mounted to an armrest that is mounted on a bed rail.
Figures 13, 14:
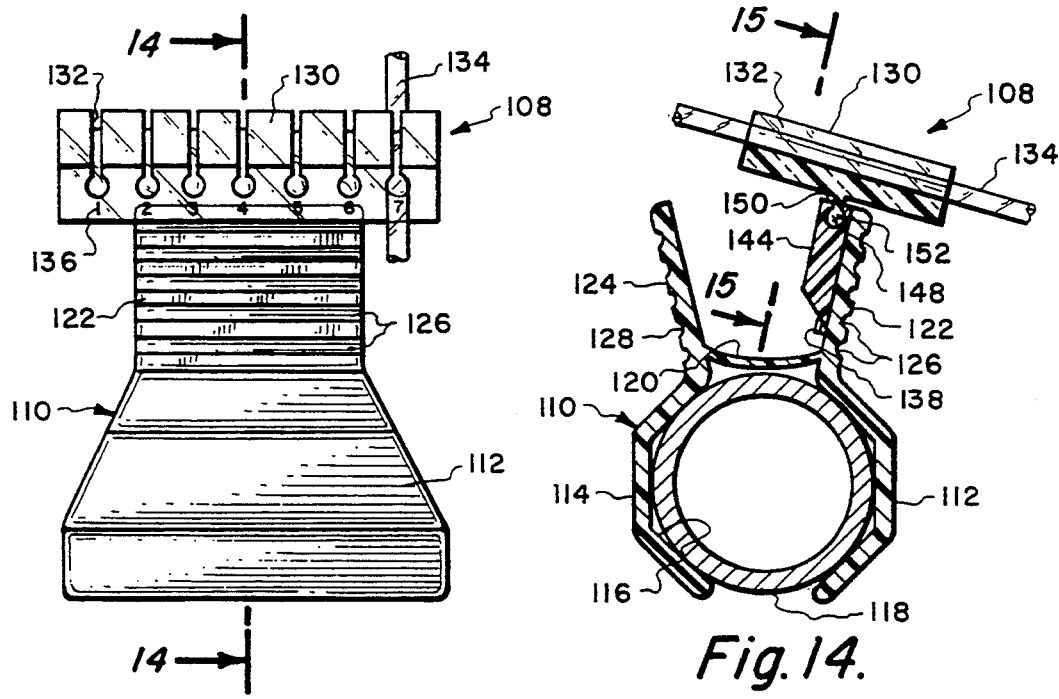
FIG. 13 is a side elevational view of a third embodiment of the line organizer of this invention.
FIG. 14 is a cross-sectional view taken along line 14—14 of FIG. 13.
Figures 15, 17:
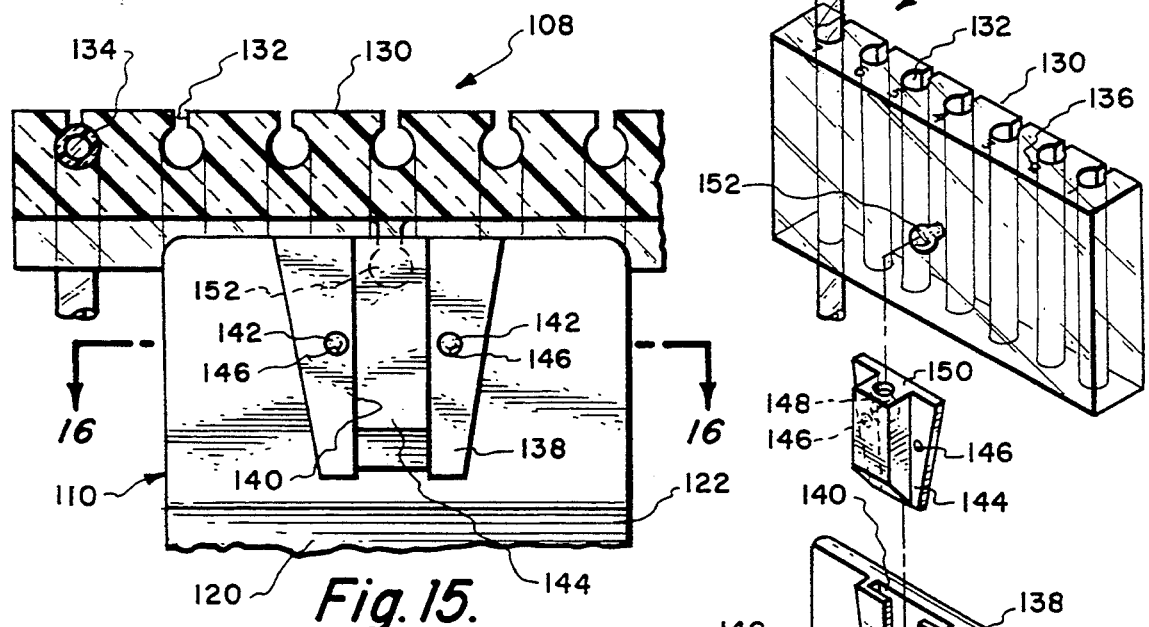
FIG. 15 is a cross-sectional view taken along line 15—15 of FIG. 14.
FIG. 17 is an exploded isometric view of the third embodiment of this invention.
Figure 16:
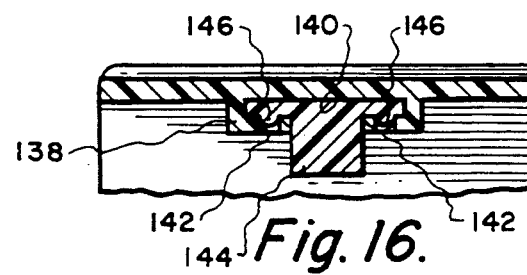
FIG. 16 is a cross-sectional view through the handle upon which the line organizer block of the third embodiment of this invention is mounted taken along line 16—16 of FIG. 15.

Referring particularly to FIG. 11 there is shown a further embodiment 86 of line organizer of this invention. The line organizer 86 is to include in a similar manner a block 88 within which are retained a plurality of lines 90. Within the lower surface of the block 88, there is mounted a plug 92 with the block 88 being readily pivotable relative to the plug 92. Within the plug 92 is located a rivet 94 with this rivet being secured to a mounting plate 96. Fixedly secured to one end of the mounting plate 96 is a jaw 98. Pivotly mounted to the opposite end of the plate 96 is a second jaw 100. The inside surface of the jaw 100 will normally include a non-metallic layer 102 of material that is impregnated with metallic slivers that have been magnetized. The layer 102 is to exert a magnetic force in conjunction with the bed rail 104 which functions to securely hold in position the clamping apparatus 106 formed by jaws 98 and 100. Manual movement of the jaw 100 in a direction away from the bed rail 104, overcoming the magnetic attraction force of the layer 102 will cause the clamping apparatus to be moved to the unsecured position permitting disconnection of the embodiment 86 from the bed rail 104 when such is deemed to be desired.

Referring particularly to FIGS. 13 to 17 of the drawings, there is shown the third embodiment 108 of line organizer of this invention. The third embodiment 108 includes a clamping apparatus 110 which is constructed of a pair of jaws 112 and 114. Jaws 112 and 114 are basically similar to jaws 24 and 26. Jaws 112 and 114 are basically identical to each other and are located in a facing relationship forming a clamping section 116 there between. The inner surface of the jaws 112 and 114 could be covered with a frictional layer of material which is not shown such as is desired. The jaws 112 and 114 are designed to establish a tight frictional connection to an exterior structure such as a cylindrically-shaped bed rail 118.

Jaws 112 and 114 are connected together by an arcuate leaf spring. The leaf spring 120 could be constructed of a metallic material and be made separate from the jaws 112 and 114 or could be constructed of a plastic material and made integral with the jaws 112 and 114. It is to be noted that the bow in the leaf spring 120 is arranged to be convex relative to the bed rail 118. It has been discovered that this bowing of the leaf spring 120 in the direction convex toward the bed rail 118 produces the greatest amount of force between the jaws 112 and 114 while maintaining the size of the leaf ring 120 as small as possible. Also, this bowing arrangement of the leaf ring 120 is so as to provide the greatest amount of clearance between the handles 122 and 124. Handle 122 is integral to jaw 112 with handle 124 being integral to jaw 114.

The exterior configuration of the handle 122 is hiatused forming a series of lineal spaced-apart grooves 126. A similar series of grooves 128 are formed within the exterior surface of the handle 124. It is the function of the grooves 126 and 128 to facilitate manual grasping and moving of the handles 122 and 124 toward each other which will permit disengagement of the jaws 112 and 114 from the bed rail 118. This movement of the jaws 112 and 114 will also be for the purpose of installing the clamping apparatus 110 on the bed rail 118.

The line organizer, which comprises block 130, is basically similar to what was previously described in relation to block 12. The line organizer 130 will normally be constructed of plastic or rubber material with it being important that the material for construction will permit a certain amount of slight deflection. Formed within the block 130 are a plurality of slots 132 with seven in number of such slots being shown. The slots 132 are located in a parallel, evenly spaced-apart relationship. Slots 132 are open ended. The slots 132 can be of the same cross-sectional size or can be of different cross-sectional sizes.

Each slot 132 defines a lower enlarged section, generally circular, and a necked-down area providing access into the lower enlarged section. A line such as tube 134 is to be slipped into a slot 132 with this slot 132 deflecting by slightly expanding until the tube 134 is located within the lower enlarged section in a close fitting manner. The tube 134 will be snugly retained within the enlarged section of the slot 132. However, a longitudinal sliding movement of the tube 134 relative to the slot 132 will be permitted.

It is to be understood that the tube 134 can comprise any kind of liquid-conducting tube, wire, catheter, or any other desired type of line. Again, the tubes 134 are to be conducted from a source (not shown) to a terminating location (not shown).

In order to again organize each of the tubes 134, each tube 134 will normally include some type of a label with indicia in the form of a series of numbers or letters or actually names (not shown). In order to assist the user in determining which tube is which tube, there is included on the block 130 a specific numerical indicia for each slot 132. This numerical indicia is defined as a series of numbers 1 through 7 and is referred to as 136 in the drawings.

Mounted on the inside surface of the handle 122 is a female section 138 of a dovetailed slot bracket. This female section 138 includes a longitudinally tapered slot 140. The section 138 includes a pair of legs with a hole 142 being formed within each leg. A male section 144 of the dovetailed bracket is to be snugly located within the female section 138. The male section 144 includes side flanges and on each side flange is located a protuberance 146. When the male section 144 is completely installed within the female section 138, a protuberance 146 is located within a hole 142 with there being established a locking detent arrangement between the male section 144 and the female section 138. It is of course to be understood that by application of sufficient manual force in an upward direction to the male section 144, it can be removed from the female section 138.

The male section 144 also includes a socket 148 on its outer or upper face 150. A ball 152 is mounted on the block 130. The ball 152 is to be snappingly engaged with the socket 148 which will securely hold in place the line organizer block 130, but yet permit pivoting or rotation thereof relative to the male section.

What is claimed is:

1. An organizer for a plurality of flexible lines comprising:
   a clamping apparatus defining a clamping section adapted for secure mounting onto an exterior structure, said clamping apparatus being movable between an unsecured position and a secured position, said secured position being when said clamping apparatus is fixed to the exterior structure, said unsecured position being when said clamping apparatus is not attached to the exterior structure, said clamping apparatus comprising a pair of jaws, a handle connected to each said jaw with there being two in number of said handles, a biasing means connected between said handles exerting a continuous biasing force tending to locate said clamping apparatus in said secured position; and
   a block mounted by mounting means on one of said jaws, said block being spaced from said clamping section, said mounting means permitting pivotal movement of said block on said clamping apparatus so as to be pivotable to various angular positions relative to said clamping apparatus, said block having a plurality of spaced-apart slots, each said slot to connect with a said line in a removably engaged manner.

2. The organizer as defined in claim 1 wherein:
   each said jaw having a handle, said mounting means being mounted on one of said handles.

3. The organizer as defined in claim 2 wherein:
   said mounting means including a ball and socket arrangement which permits the pivoting of said block relative to said clamping apparatus.

4. The organizer as defined in claim 3 wherein:
   said mounting means further includes a dovetailed bracket assembly, said dovetailed bracket assembly being locatable in an engaged position and a disengaged position, said disengaged position resulting in separation of said block and said ball and socket from said clamping apparatus.

5. The organizer as defined in claim 4 wherein:
   said dovetailed bracket assembly including a locking detent to securely connect together said block and said clamping apparatus when in said engaged position.

6. The organizer as defined in claim 5 wherein:
   a biasing means located between said handles, said biasing means exerting a continuous force tending to locate said clamping apparatus in said secured position.

7. The organizer as defined in claim 6 wherein:
   said biasing means comprising a leaf spring.

8. The organizer as defined in claim 7 wherein:
   said block including a series of differentiating indicia with there being a specially different indicia for each said slot, said lines including a similar series of said indicia, a said line to be located within a slot with their indicia corresponding.

* * * * *